US009474452B2

(12) United States Patent
Kochs et al.

(10) Patent No.: US 9,474,452 B2
(45) Date of Patent: Oct. 25, 2016

(54) METHOD AND SYSTEM FOR QUANTIFYING ANAESTHESIA OR A STATE OF VIGILANCE

(75) Inventors: Eberhard F. Kochs, Munich (DE); Gerhard Schneider, Duesseldorf (DE); Denis Jordan, Munich (DE); Adem Omerovic, Munich (DE); Matthias Kreuzer, Munich (DE)

(73) Assignee: Technische Universitaet Muenchen, Munich (DE)

( * ) Notice: Subject to any disclaimer, the term of this patent is extended or adjusted under 35 U.S.C. 154(b) by 352 days.

(21) Appl. No.: 14/124,024

(22) PCT Filed: May 21, 2012

(86) PCT No.: PCT/EP2012/002158
§ 371 (c)(1),
(2), (4) Date: Dec. 5, 2013

(87) PCT Pub. No.: WO2012/171610
PCT Pub. Date: Dec. 20, 2012

(65) Prior Publication Data
US 2014/0155706 A1    Jun. 5, 2014

(30) Foreign Application Priority Data

Jun. 17, 2011  (DE) .................. 10 2011 104 449
Aug. 19, 2011  (EP) ..................... 11178111

(51) Int. Cl.
*A61B 5/00* (2006.01)
*A61B 5/0484* (2006.01)
(Continued)

(52) U.S. Cl.
CPC ............ *A61B 5/0205* (2013.01); *A61B 5/021* (2013.01); *A61B 5/02405* (2013.01);
(Continued)

(58) Field of Classification Search
None
See application file for complete search history.

(56) References Cited

U.S. PATENT DOCUMENTS 5,372,140 A * 12/1994 Pomfrett .............. A61B 5/0205
                                                         600/484
5,458,117 A * 10/1995 Chamoun .............. A61B 5/048
                                                         600/547
(Continued)

FOREIGN PATENT DOCUMENTS

EP     1495715 A1    1/2005
WO    02100267 A1   12/2002

OTHER PUBLICATIONS

Bandt, et al. "Permutation Entrophy: A Natureal Complexity Measure for Time Series." The American Physical Society, vol. 88, No. 17, Apr. 29, 2002. 4 Pages.
(Continued)

*Primary Examiner* — Brian T Gedeon
(74) *Attorney, Agent, or Firm* — Eschweiler & Associates, LLC

(57) ABSTRACT

A method and a system for quantifying anaesthesia and/or a state of vigilance (e.g. monitoring sedation or sleep) from a plurality of parameters acquired from a subject allows to determine an indicator that reliably quantifies the hypnotic component of anaesthesia and/or the state of vigilance and/or the analgesic component of anaesthesia, even if the number of parameters varies while monitoring the subject. Preferably, a first sub-indicator based on a first subset of parameters adapted to characterize a boundary region between consciousness and unconsciousness is determined, and a second sub-indicator based on a second subset of parameters adapted to characterize a level of hypnosis of said subject is determined, and said first sub-indicator and said second sub-indicator are then combined to compute a global indicator value.

15 Claims, 8 Drawing Sheets

(51) Int. Cl.
*A61B 5/0402* (2006.01)
*A61B 5/145* (2006.01)
*A61B 5/0205* (2006.01)
*A61B 5/021* (2006.01)
*A61B 5/024* (2006.01)
*A61B 5/08* (2006.01)

(52) U.S. Cl.
CPC .......... *A61B 5/04845* (2013.01); *A61B 5/145* (2013.01); *A61B 5/4821* (2013.01); *A61B 5/4848* (2013.01); *A61B 5/7267* (2013.01); *A61B 5/742* (2013.01); *A61B 5/0402* (2013.01); *A61B 5/082* (2013.01); *A61B 5/7278* (2013.01)

(56) References Cited

U.S. PATENT DOCUMENTS

| | | | | |
|---|---|---|---|---|
| 6,120,443 | A * | 9/2000 | Cohen-Laroque | A61B 5/00 128/897 |
| 6,431,171 | B1 * | 8/2002 | Burton | A61M 15/00 128/204.18 |
| 6,496,724 | B1 * | 12/2002 | Levendowski | A61B 5/048 128/920 |
| 6,575,902 | B1 * | 6/2003 | Burton | A61B 5/18 340/575 |
| 6,625,485 | B2 * | 9/2003 | Levendowski | A61B 5/048 128/920 |
| 6,685,649 | B2 * | 2/2004 | Korhonen | A61B 5/0456 600/485 |
| 6,868,345 | B1 * | 3/2005 | Jensen | A61B 5/4821 702/188 |
| 7,215,994 | B2 * | 5/2007 | Huiku | A61B 5/0476 600/544 |
| 7,367,949 | B2 * | 5/2008 | Korhonen | A61B 5/1106 600/481 |
| 7,407,485 | B2 * | 8/2008 | Huiku | A61B 5/0456 600/300 |
| 7,565,905 | B2 * | 7/2009 | Hickle | A61M 16/0084 128/200.24 |
| 7,774,052 | B2 * | 8/2010 | Burton | A61B 5/0476 600/544 |
| 7,937,138 | B2 * | 5/2011 | Liley | A61B 5/048 600/544 |
| 8,096,946 | B2 * | 1/2012 | Burton | A61B 5/18 340/575 |
| 8,463,370 | B2 * | 6/2013 | Korhonen | A61B 5/1106 600/544 |
| 8,641,632 | B2 * | 2/2014 | Quintin | A61B 5/0205 600/481 |
| 8,864,702 | B2 * | 10/2014 | Chazot | A61M 5/1723 604/66 |
| 8,977,504 | B2 * | 3/2015 | Hovorka | G06F 19/3437 702/19 |
| 2002/0117176 | A1 * | 8/2002 | Mantzaridis | A61B 5/1106 128/204.23 |
| 2005/0010116 | A1 | 1/2005 | Korhonen et al. | |
| 2007/0167694 | A1 * | 7/2007 | Causevic | A61B 5/0402 600/301 |
| 2008/0242955 | A1 * | 10/2008 | Uutela | A61B 5/021 600/301 |
| 2011/0015468 | A1 * | 1/2011 | Aarts | A61B 5/0205 600/26 |
| 2011/0118619 | A1 | 5/2011 | Burton et al. | |
| 2011/0125046 | A1 * | 5/2011 | Burton | A61B 5/0476 600/544 |
| 2012/0179008 | A1 * | 7/2012 | Burton | A61B 5/18 600/301 |

OTHER PUBLICATIONS

International Search Report & Written Opinion of the International Searching Authority dated Sep. 27, 2012 for International Application No. PCT/EP2012/002158. 11 Pages.

* cited by examiner

METHOD AND SYSTEM FOR QUANTIFYING ANAESTHESIA OR A STATE OF VIGILANCE

FIELD OF THE INVENTION

The present invention relates to a method and system for quantifying anaesthesia (such as a hypnotic component of anaesthesia, a depth of anaesthesia, detection of intraoperative awareness, and/or an analgesic component of anaesthesia) and/or a state of vigilance (e.g. monitoring sedation or sleep) in an human or animal patient.

BACKGROUND AND RELEVANT STATE OF THE ART

Anaesthesia is generally considered to have four main components: hypnosis (reversible state of unconsciousness), amnesia (repression of memory), analgesia (pain relief) and stable innervation of the autonomic nervous system. In practice, anaesthesia is achieved by combining several different anaesthetics and/or sedatives, wherein each of the components has specific effects on one or several of the above-mentioned components.

During anaesthesia, for adequate hypnosis, patients must be carefully and continuously monitored to achieve an appropriate balance between delivery of too high or too low concentrations of hypnotic agents. Delivery of too low doses of the hypnotic agent(s) may result in a patient being aware of what is happening during a procedure and possibly a later recall of the procedure, whereas too high doses of the hypnotic agent(s) may involve the risk of damage to the patient's central nervous system, or may result in sickness after the procedure or in a delayed convalescence.

Conventionally, so-called surrogate standard parameters such as blood pressure, heart frequency, perspiration and/or lacrimation have been employed to monitor the patient's state of anaesthesia during a procedure or surgery. These surrogate parameters do not provide a direct measure of depth of anaesthesia, as they do not reflect the main target organ of anaesthesia, namely the brain, and they are affected by other drugs and surgery. Electroencephalographic (EEG) signals have been employed to achieve a more specific monitoring of the state of the brain during anaesthesia, as the brain is the target organ of hypnosis. Specific parameters are extracted from the rather complex EEG signal to provide a quantitative measure of the hypnotic component of anaesthesia, in particular to distinguish between consciousness and unconsciousness. By employing several EEG parameters, the specific states of consciousness associated with the level of anaesthesia may be distinguished with a greater degree of reliability. Commercial EEG anaesthesia monitors of this type are available, e.g. under the name "BIS" from Aspect Medical Systems, Inc., USA and Covidien plc, Ireland, "Entropy Module" from GE Healthcare, USA, and "Narcotrend" from MHH, Germany. In these systems, "depth of anaesthesia" is generally quantified by means of a scalar indicator ranging between 0 and 100, with values between 0 and 20 corresponding to deep anaesthesia and values between 80 and 100 corresponding to consciousness/wakefulness.

In order to further enhance the reliability and accuracy of anaesthesia monitoring, there have been attempts to combine EEG parameters with standard parameters into a single indicator.

For instance, US 2007/0167694 A1 discloses a method and an apparatus for anaesthesia and sedation monitoring in which an index value representative of a condition of a patient may be computed by integrating EEG, pulse oxymetry, ECG and auditory evoked potential (AEP) signals.

European patent application EP 1 495 715 A1 describes a method and an apparatus for analgesia monitoring based on a mathematical index that combines three physiological parameters. These parameters may comprise blood pressure, cardiac excitation, ECG and EEG data, where EEG includes EMG data. EEG and EMG data may be analysed by means of spectral entropic quantities, and the mathematical index may be based on a fuzzy rule-based reasoning procedure.

International patent application WO 02/100267 discloses a method and a system for monitoring the depth of anaesthesia that is based on both EEG parameters and an AEP analysis, and may take into account certain patient data such as age, weight, height and gender.

However, these methods and systems generally suffer from the disadvantage that their algorithms rely on a fixed and predetermined number of input parameters in order to provide a reliable estimate of the state of anaesthesia. In an operating theatre, it often happens that data acquisition of one or more of these parameters becomes unreliable or fails completely. For instance, failure of EEG data acquisition is a common problem in conventional monitoring systems, and may lead to the monitoring apparatus being switched off automatically, or at least to inaccurate readings. The medical personnel may then be left without an accurate indication of the patient's hypnotic state. In stress or emergency situations that are common in hospitals, especially in an operating theatre, this may result in the patient receiving inadequate anaesthetic doses, with the detrimental consequences described above. Similar problems are encountered in the monitoring of vigilance.

Hence, what is needed is a method and a system for quantifying the depth of anaesthesia that provides a greater level of accuracy and reliability.

OVERVIEW OF THE PRESENT INVENTION

This objective is achieved with a method and a system for quantifying anaesthesia and/or a state of vigilance with the features of independent claims 1 and 13, respectively. The depend-ent claims relate to preferred embodiments.

The method according to the present invention comprises the steps of acquiring a plurality of p parameters pertaining to a subject under survey, said parameters being selected from a first parameter group comprising electrocardiogram data acquired from said subject, a heart rate, a heart rate variability, a blood pressure, a blood pressure variability, a breathing gas composition, a pharmacokinetic/pharmacodynamic modelled effect site concentration and/or plasma concentration, and/or from a second parameter group comprising electroencephalogram data and/or auditory evoked potential data acquired from said subject, and/or from a third parameter group comprising subject data and/or medication data, wherein $p \geq 2$ and at least one of said p parameters is selected from said first parameter group or said second parameter group, wherein said parameters of said first parameter group and/or said parameters of said second parameter group are acquired continuously or at predetermined time intervals by monitoring said subject. The method further comprises the step of determining an indicator that quantifies a hypnotic component of anaesthesia i.e. a depth of anaesthesia and/or detects an intraoperative awareness and/or quantifies an analgesic component of anaesthesia, or a state of vigilance of said subject from said p parameters, wherein said step of determining said indicator comprises the step of combining said p parameters, wherein said number p of parameters is variable while monitoring said subject.

Hence, the present invention provides a method in which the number of p parameters selected from among said first, second, and/or third group(s) is allowed to vary or may vary while monitoring said subject. By providing a method for quantifying the hypnotic component of anaesthesia and/or the state of vigilance and/or the analgesic component of anaesthesia in which the number of parameters is not fixed or predetermined, the method according to the present invention may accommodate situations in which data acquisition of one or more parameters fails during the monitoring of a subject, and still provides an indicator that characterizes the hypnotic component of anaesthesia and/or the state of vigilance and/or the analgesic component of anaesthesia with a high degree of accuracy.

In a preferred embodiment, said step of combining said p parameters comprises the step of employing an adaptive neuro fuzzy inference system and/or a neural network and/or regression and/or support vector machines and/or statistical relational machine learning (with or without involving adaptive algorithms for online training). The inventors found that these techniques are particularly suited to accommodate a variable number of parameters. They can be extended with specific algorithms such that they do not require a fixed number of parameters as an input, and may still provide meaningful results even if the number of parameters changes while monitoring said subject, for instance due to failure of EEG data.

The so-called TSK model (named after Takagi Sugeno Kang) is an adaptive neuro fuzzy inference system that is particularly suited to accommodate a variable number of parameters by using algorithms for inherent parameter imputation and/or replacement.

In a preferred embodiment, the method comprises the step of determining the quality of parameter values by means of an automatic artefact identification.

In a further preferred embodiment, the method comprises the step of replacing a parameter that becomes unavailable, either temporarily or permanently, by means of a model based replacement using initialized values or ranges of values, an average value imputation, univariate regression from previously recorded parameter values, multivariate regression from previously recorded parameter values, or matching of an incomplete parameter vector with a complete vector of previously recorded parameter values.

Missing parameter values may likewise be replaced by means of a prediction employing a K-nearest neighbour model, a self-organising map, multi-layer perception, or recurrent neural network techniques.

The indicator may then be determined in terms of the remaining parameter values and the model-inherent replacement values or imputed values generated by one or all of the techniques described above.

In a further possible embodiment, the method comprises the step of prediction and smoothing the indicator time series. Unreliable parameter values caused by artefacts may induce fluctuations in indicator time series which are not related to the physiological state of the patient. Multivariate techniques of time series prediction and smoothing employing Kalman filters, neuronal networks or adaptive median filters (e.g. weighted repeated median filters) are particularly suited for prediction or smoothing of the indicator values.

The indicator may preferably be a scalar quantity.

In a preferred embodiment, at least one parameter among said p parameters is chosen from said second parameter group.

Preferably, $p \geq 3$, and at least one parameter among said p parameters is chosen from each of said first, second, and third parameter group.

The inventors found that by combining at least one parameter relating to electroencephalogram data with at least one parameter relating to standard monitoring, medication protocol and concentration and/or subject data, particularly reliable results in quantifying the hypnotic component of anaesthesia can be achieved. The inclusion of subject data allows to determine an indicator that is well adapted to the individual subject under survey.

Said first parameter group may comprise a systolic blood pressure, a diastolic blood pressure, a mean blood pressure, an inspiratory oxygen concentration, an expiratory oxygen concentration, an expiratory $CO_2$ concentration, an inspiratory anaesthetic gas concentration, an expiratory anaesthetic gas concentration, a pharmacokinetic/pharmacodynamic modelled effect site concentration and/or a plasma concentration, parameters of a heart rate variability, parameters of blood pressure variability, preferably an approximate entropy of a heart rate and/or a blood pressure variability, and/or an ordinal permutation entropy of a heart rate and/or a blood pressure variability, and/or relative time deviations of said parameters of said first parameter group.

Said second parameter group may comprise an approximate entropy computed from said electroencephalogram data, an ordinal permutation entropy computed from said electroencephalogram data, a symbolic transfer entropy computed from said electroencephalogram data, a weighted spectral median frequency (WSMF) computed from said electroencephalogram data, a burst suppression (BS) ratio computed from said electroencephalogram data, statistical parameters such as moments computed from said electroencephalogram data and/or from said auditory evoked potential data, absolute and relative band power computed from said electroencephalogram data and/or from said auditory evoked potential data, first and/or higher order spectral parameters computed from said electroencephalogram data and/or from said auditory evoked potential data, wavelet parameters computed from said electroencephalogram data and/or from said auditory evoked potential data, recurrence analysis parameters such as recurrence rate computed from said electroencephalogram data and/or from said auditory evoked potential data, phase space analysis parameters such as dimensions computed from said electroencephalogram data, and symbolic order pattern analysis parameters computed from said electroencephalogram data.

Said electroencephalogram data may comprise electromyographic (EMG) signals. This may be advantageous for evaluating a signal-to-noise ratio of electroencephalographic data and to quantify muscle activity as a supplemental information of the patient's state during anaesthesia.

EMG signals typically have most of their energy in a frequency range from about 40 Hz to 300 Hz, which is different from the frequency range of the standard EEG parameters. Hence, alternatively, the electrocardiogram data may be filtered to reduce the impact of EMG signals on the EEG signals if awareness is to be detected and relaxation effects shall not be included.

In a preferred embodiment, at least one of said parameters is selected from said second parameter group, comprising an ordinal permutation entropy computed from said electroencephalogram data and/or a symbolic transfer entropy computed from said electroencephalogram data. The inventors found that by including ordinal permutation entropy and/or symbolic transfer entropy in the analysis, electroencephalogram data can be analysed more efficiently. Reliable results can be obtained from shorter segments of EEG raw data, and hence the depth of anaesthesia, in particular awareness, can be determined more reliably and more quickly. The inventors found that good results can be achieved with data acquisition times of below 20 seconds, preferably 1 to 10 seconds.

Said third parameter group may comprise gender, age, weight and a body mass index of said subject, and/or may comprise the type of surgery or procedure to be performed on said subject, and/or may comprise a drug protocol of anaesthetics to be administered to said subject.

In a preferred embodiment, said parameters from said third parameter group may be read from a database.

It is to be understood that the method and the system according to the present invention do not need to provide or to be capable of processing all the parameters in the first, second, and third parameter groups, respectively. These are mere examples among which suitable parameters can be selected for analysis, depending on the preferences of those skilled in the art and the particulars of the type of surgery or analysis to be performed.

It is also to be understood that the first, second, and third parameter group may comprise further parameters that may not be listed above, but are nevertheless suitable for characterising the hypnotic component of anaesthesia and/or the state of vigilance and/or the analgesic component of anaesthesia.

In the context of the present invention, a "parameter" may be used as a synonym for the value of said parameter.

In a preferred embodiment, the method according to the present invention comprises the steps of selecting the parameters from the first parameter group and/or second parameter group depending on the parameters selected from the third parameter group, in particular depending on the gender and/or the age of said subject and/or medication data and/or the type of procedure or surgery to be performed on the subject. This allows to adapt the method for quantifying anaesthesia and/or a state of vigilance to the subject under investigation, and/or to the type of surgery to be performed, as well as to take into account the anaesthetic or sedative employed. On the one hand, this may lead to a more specific and hence more reliable analysis of the state of anaesthesia and/or vigilance. On the other hand, the method according to the preferred embodiment may reduce the complexity of the computation of the indicator, since only those parameters that are essential for the particular subject and/or type of surgery under consideration are included in the analysis. Reliable results may hence be obtained more quickly.

In a preferred embodiment, said step of combining said p parameters comprises the step of comparing said p parameters against a model based on previously acquired training data. The training data may be data of subjects whose state of anaesthesia was determined and for which corresponding parameter values were monitored and were associated with the state of anaesthesia.

In a preferred embodiment, said step of determining said indicator comprises the step of determining a first sub-indicator based on a first subset of parameters chosen among said p parameters, and/or based on a comparison of acquired parameters with a first training set of data, wherein said first sub-indicator is adapted to characterise a first aspect of an anaesthesia or vigilance state of said subject, and further comprises the step of determining a second sub-indicator based on a second subset of parameters chosen among said p parameters, and/or based on a comparison of acquired parameters with a second training set of data, said second subset of parameters being different from said first subset of parameters, and/or said second training set of data being different from said first training set of data, wherein said second sub-indicator is adapted to characterise a second aspect of an anaesthesia or vigilance state of said subject, and combining said first sub-indicator and said second sub-indicator to compute said indicator. The first and second aspect of anaesthesia may be any aspect or any state of the subject that is suitable to characterize the hypnotic component of anaesthesia and/or the state of vigilance and/or an analgesic component of anaesthesia.

The inventors found that particularly reliable results can be obtained by determining first and second sub-indicators first, and then combining these sub-indicators into a global indicator in a subsequent step. Successive computation of the indicator from sub-indicators allows to make a suitable choice of parameter sets and individual models for the first sub-indicator and the second sub-indicator individually from parameters that are known to be particularly suitable to characterise the first and the second aspect of anaesthesia, respectively. This allows to take expert knowledge into account for the modelling, and may significantly reduce the complexity of the subsequent step of determining the indicator. As a result, the indicator can be determined with a greater degree of reliability. At the same time, the determination of the indicator from sub-indicators in a two-step procedure makes the method more robust against a failure of individual parameter readings. Depending on the individual model or paradigm, some parameter values may be less essential for the analysis, and hence the analysis will be affected only marginally if one of these parameter values becomes unavailable. If one specific parameter value becomes unavailable due to a failure in the monitoring, this will typically affect only one of the sub-indicators. Even if the parameter affects both sub-indicators, it will usually do so to different degree or extent. Reliable results can then still be obtained from the sub-indicator that is less affected or not affected at all.

In a preferred embodiment, said first subset and said second subset of parameters may be not identical. However, it is understood that the first subset and the second subset may have one or more or all parameters in common.

In a preferred embodiment, said first aspect may be a boundary region between consciousness and unconsciousness of said subject. The inventors found that this is a region that requires particularly close survey and is crucial for reliable and accurately timed detection of consciousness and for determining the anaesthetic concentrations that should be administered to the subject in order to avoid intraoperative awareness in said subject.

Said first subset may comprise electroencephalogram data, in particular an ordinal permutation entropy computed from said electroencephalogram data and/or a symbolic transfer entropy computed from said electroencephalogram data, and a weighted spectral median frequency computed from said electroencephalogram data. Said first subset may further comprise a breathing gas composition, in particular an inspiratory oxygen concentration, an expiratory oxygen concentration, an expiratory $CO_2$ concentration, an inspiratory anaesthetic gas concentration, an expiratory anaesthetic gas concentration, a pharmacokinetic/pharmacodynamic modelled effect site concentration and/or plasma concentration, electrocardiogram data and/or an approximate entropy of a heart rate variability, and/or an ordinal permutation entropy of a heart rate variability. Said first subset may also comprise subject data and/or medication data. The training of the said first sub-indicator with respect to said first subset of data is particularly oriented to the first aspect of anaesthesia.

Said second aspect may be an overall level of anaesthesia of said subject, in particular a level of hypnosis from wakefulness to deep anaesthesia of said subject.

Said second subset may particularly comprise electroencephalogram data, in particular an approximate entropy, an ordinal permutation entropy computed from said electroencephalogram data, and a burst suppression ratio computed from said electroencephalogram data. Said second subset may further comprise a breathing gas composition, in particular an inspiratory oxygen concentration, an expiratory oxygen concentration, an expiratory $CO_2$ concentration, an inspiratory anaesthetic gas concentration, an expiratory anaesthetic gas concentration, a pharmacokinetic/parmacodynamic modelled effect site concentration and/or plasma concentration, electrocardiogram data and/or an approximate entropy of a heart rate variability, and/or an ordinal permutation entropy of a heart rate variability. Said second subset may also comprise subject data and/or medication data. The training of the said second sub-indicator with respect to said second subset of data is particularly oriented to the second aspect of anesthesia.

The method according to the present invention is not limited to two sub-indicators, but may comprise further sub-indicators based on further subsets of training data and/or subsets of parameters to characterise further aspects of anaesthesia and/or vigilance and/or analgesia and/or to characterize patient individual modelling (age range, gender, drug protocol), wherein all these sub-indicators may be combined to compute said indicator of the hypnotic component of anaesthesia and/or the state of vigilance and/or the analgesic component of anaesthesia.

In a preferred embodiment, said step of determining said indicator comprises the step of determining a third sub-indicator based on a third subset of parameters chosen among said p parameters, and/or based on a comparison of acquired parameters with a third training set of data, wherein said third subset of parameters is different from said first subset of parameters and/or said second subset of parameters and/or said third training set of data is different from said first training set and/or said second training set, respectively, and wherein said third sub-indicator is adapted to characterise deep anaesthesia, in particular deep hypnosis. The method according to said preferred embodiment further comprises the step of combining said first sub-indicator, said second sub-indicator, and said third sub-indicator to compute said indicator.

Said third subset may preferably comprise an approximate entropy computed from said electroencephalogram data, an ordinal permutation entropy computed from said electroencephalogram data and/or a burst suppression ratio computed from said electroencephalogram data. The inventors found that this combination of parameters is particularly suited to characterise deep anaesthesia or deep hypnosis.

In a preferred embodiment, the method according to the present invention further comprises the step of pharmacokinetic/pharmacodynamic modelling and/or of computing a dose of an anaesthetic to be administered to said subject, based on said indicator. Preferably, supply of said anaesthetic may be controlled by means of a closed-loop technique.

Preferably, the number p of parameters and/or the type of parameters are chosen in accordance with the type and/or dose of anaesthetic and/or sedative to be administered to said subject. The inventors found that the specifics of quantifying the hypnotic component of anaesthesia and/or the state of vigilance and/or the analgesic component of anaesthesia may crucially depend on the type and/or dose of anaesthetic that is administered to the subject. It is therefore advantageous to choose the set of p parameters depending on the anaesthetic, and to determine an indicator model that is specific to the type of anaesthetic.

In a preferred embodiment, the inventive method further comprises the step of recording at least one parameter value among said p parameter values and/or at least one said sub-indicator value among said sub-indicator values and/or said indicator value, and/or raw input data, in particular recording said at least one time-synchronised predefined event and/or free text comment if said indicator value is detected not to correspond to the clinically evaluated patient state by the investigator and/or if a predefined event occurs during surgery. This allows the medical personnel to record ambiguous indicator outcomes and/or exceptional events during the surgery or the procedure, so that these time points may be examined later with greater scrutiny and may be used for further improvements of the said indicator.

Preferably, the method further comprises the step of recording a plurality of parameter values among said p parameter values and/or recording raw input data in the vicinity of said ambiguous indicator outcomes and/or said exceptional events, for instance all parameter values and raw input data in a predetermined time interval around said event.

According to a preferred embodiment, the method further comprises the step of employing said p parameters and/or said raw input data acquired by monitoring said subject to modify an algorithm upon which said step of determining said indicator is based. This allows the parameter values and/or said raw input data acquired from the subject under monitoring to be employed to further train the algorithm for determining an indicator, so that the reliability of the inventive method for quantifying the hypnotic component of anaesthesia and/or the analgesic component of anaesthesia can be further improved during operation.

The invention further relates to a system for quantifying anaesthesia and/or a state of vigilance from a plurality of parameters acquired from a subject, said system comprising acquisition means adapted to acquire a plurality of p parameters pertaining to said subject, said parameters selected from a first parameter group comprising electrocardiogram data acquired from said subject, a heart rate, a heart rate variability, a blood pressure, a blood pressure variability, a breathing gas composition, a pharmacokinetic/pharmacodynamic modelled effect site concentration, and/or plasma concentration and/or a second parameter group comprising electroencephalogram data and/or auditory evoked potential data acquired from said subject, and/or a third parameter group comprising subject data and/or medication data, wherein $p \geq 2$, and at least one of said p parameters is selected from said first parameter group or said second parameter group. Said acquisition means are adapted to acquire said parameters of said first parameter group and/or said parameters of said second parameter group continuously or at predetermined time intervals, in particular by monitoring said subject. Said system further comprises calculation means adapted to determine from said p parameters an indicator that quantifies a depth of anaesthesia and/or detects intraoperative awareness, and/or quantifies an analgesic component of anaesthesia or a state of vigilance of said subject, wherein said acquisition means are adapted to acquire a number p of parameters that varies while monitoring said subject, and said calculation means are adapted to determine said indicator by combining said number p of parameters that varies while monitoring said subject.

Said system may be adapted to implement a method with some or all of the features described above.

The invention further relates to a storage device with computer-readable instructions stored thereon, adapted to implement on a computer for controlling said system, when read on said computer, a method with some or all of the features described above.

DETAILED DESCRIPTION OF PREFERRED EMBODIMENTS

The features and numerous advantages of the present invention may be understood best from a detailed description of the preferred embodiments in conjunction with the accompanying drawings, in which:

FIG. 1a schematically shows a system for monitoring a patient and quantifying the depth of anaesthesia according to a first embodiment of the present invention;

FIG. 1b schematically shows a system for monitoring a patient and quantifying the depth of anaesthesia according to a second embodiment of the present invention;

Figure 5A:
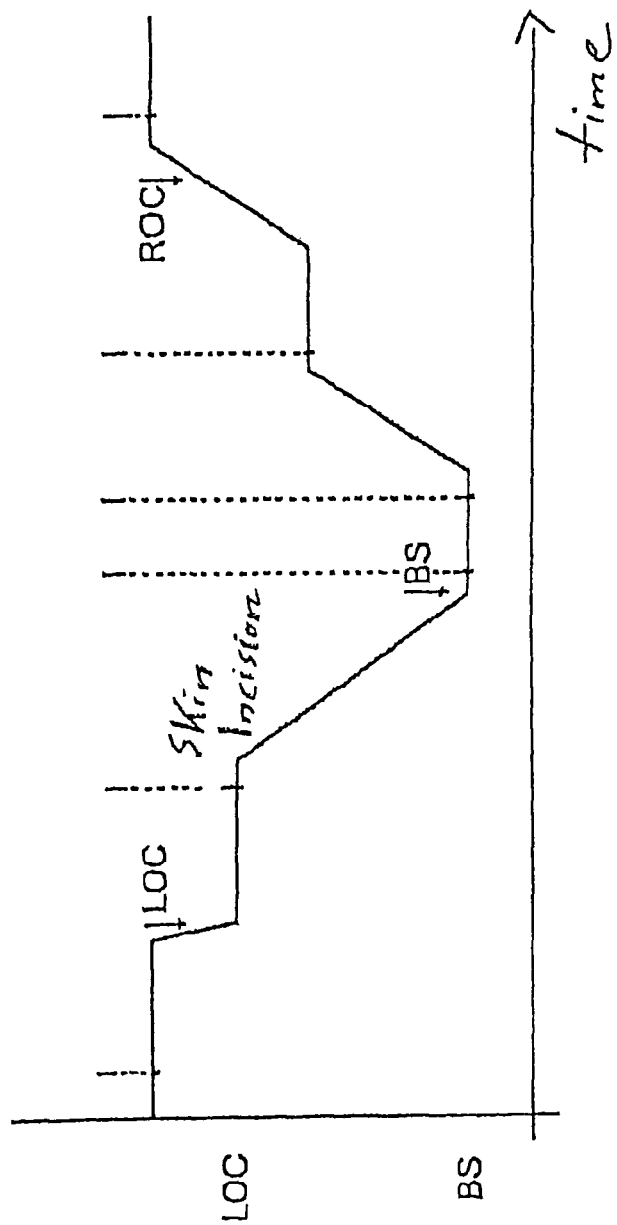
Figure 5B:
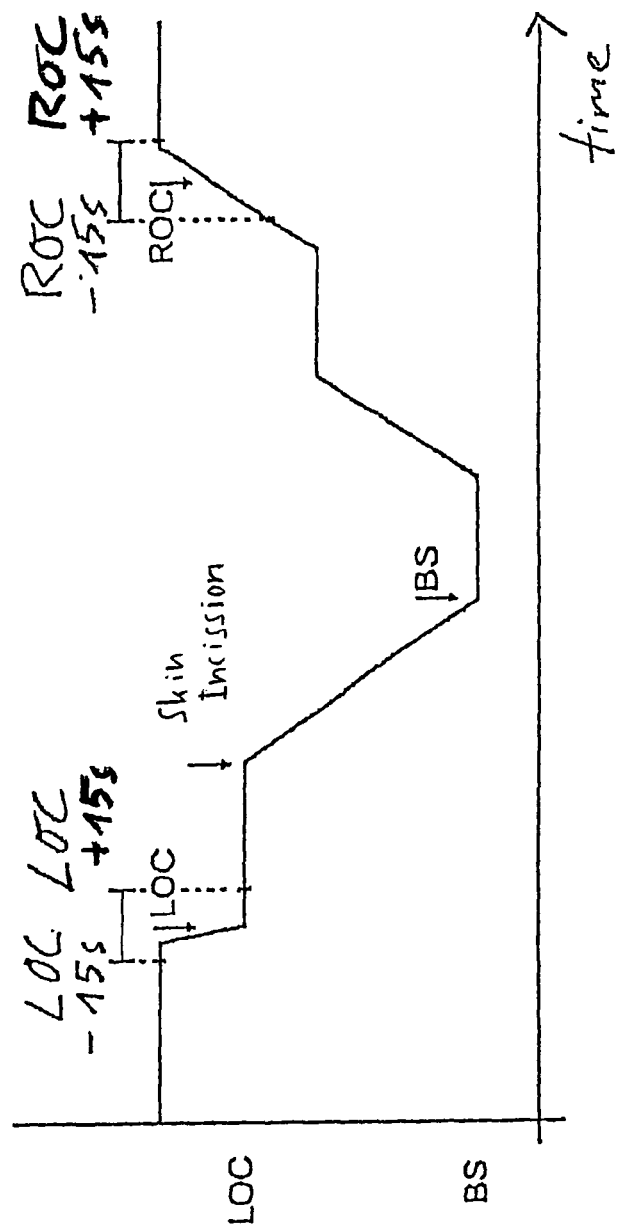
Figure 6A:
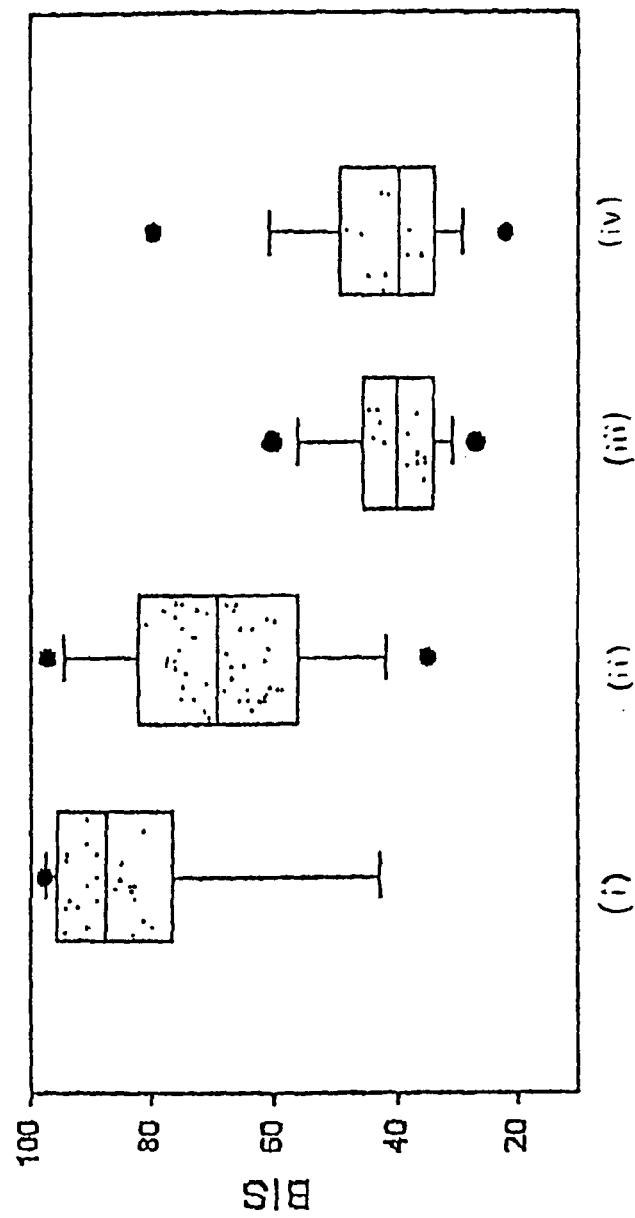
Figure 6B:
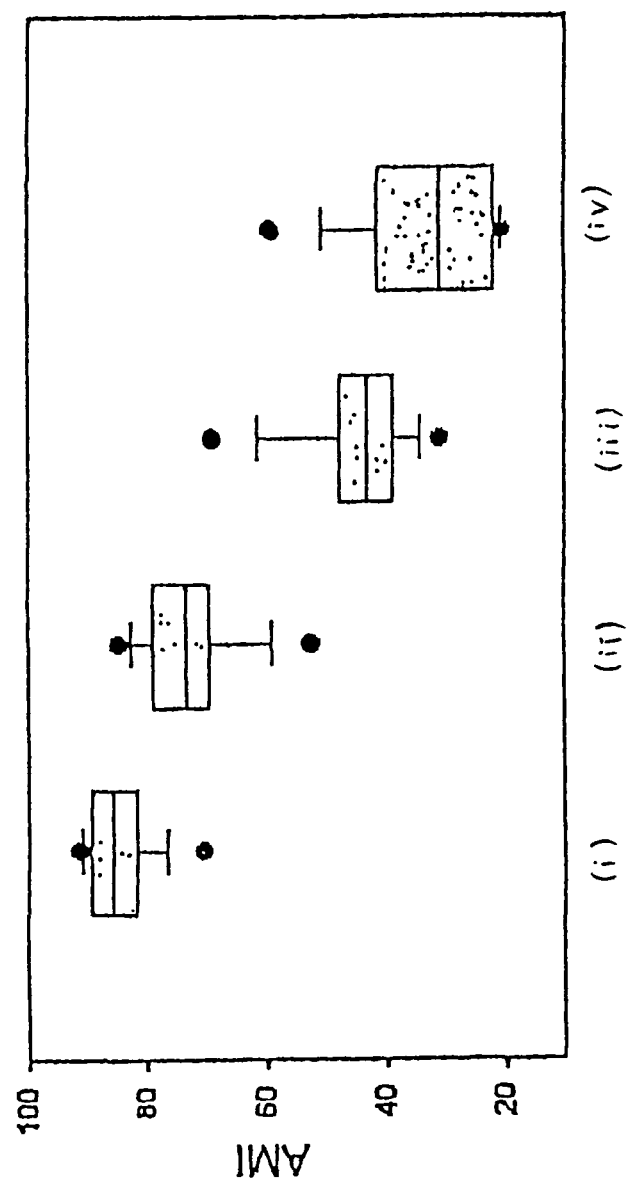

FIGS. 5a, 5b are charts that illustrate the study period over time of a patient study with specified hypnotic levels, for two different data selections used for the training and test of the first and second sub-indicator and of the indicator; and FIGS. 6a, 6b show a distribution of indicator values for the aspect "consciousness and wakefulness", "loss of consciousness", "clinical routine" and "deep anaesthesia with EEG burst suppression", determined according to the conventional BIS model (FIG. 6a) and the method according to the present invention (FIG. 6b) in comparison.

The invention will now be described with reference to a system and a method for quantifying the depth of anaesthesia of a patient in a hospital environment from a plurality of parameters selected from different parameter groups. Among these groups there are standard parameters such as electrocardiogram data, a heart rate variability, or blood pressure, as well as electroencephalogram data and patient data and/or medication data.

Figure 1A:
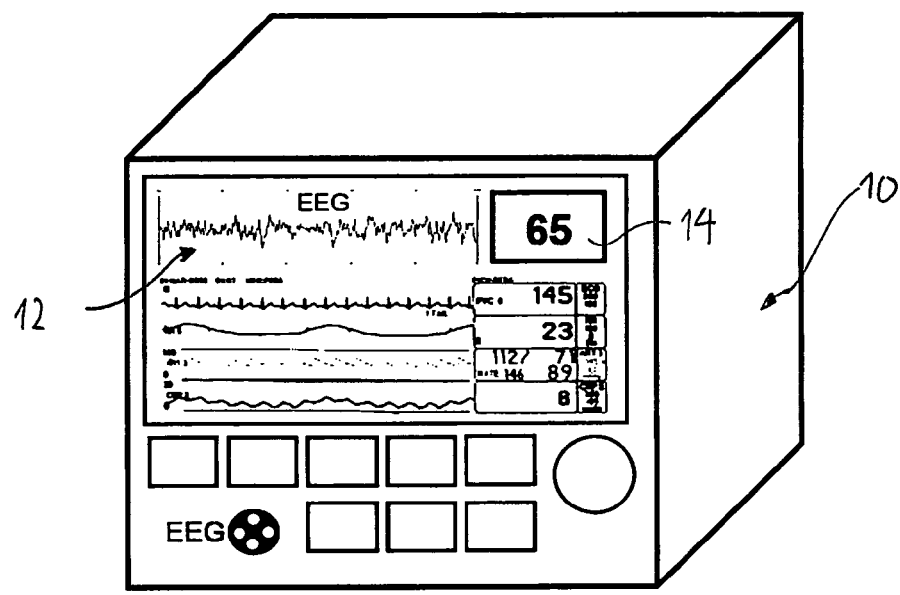

The invention can be embodied in a stand-alone monitoring system 10 as shown in FIG. 1a, which incorporates EEG data acquisition, the derivation of standard parameters with data acquired from standard monitoring of anaesthesia, such as an interface for reading subject data, a medication protocol and dosage. The stand-alone unit 10 shown in FIG. 1a also incorporates a processor for determining an indicator that quantifies the depth of anaesthesia by combining all these parameters, as will be described further below.

The anaesthesia monitor 10 comprises a display 12 for outputting standard parameters such as a heart rate, systolic or diastolic blood pressure, as well as EEG data. The display 12 also comprises an indicator output 14 which is adapted to display the value of the indicator computed from the chosen set of parameters as a scalar quantity preferably between 0 and 100 ("65" in the example shown in FIG. 1a). As described in the introductory section, values between 0 and 20 are generally associated with deep anaesthesia, whereas values between 80 and 100 correspond to consciousness/wakefulness.

Figure 1B:
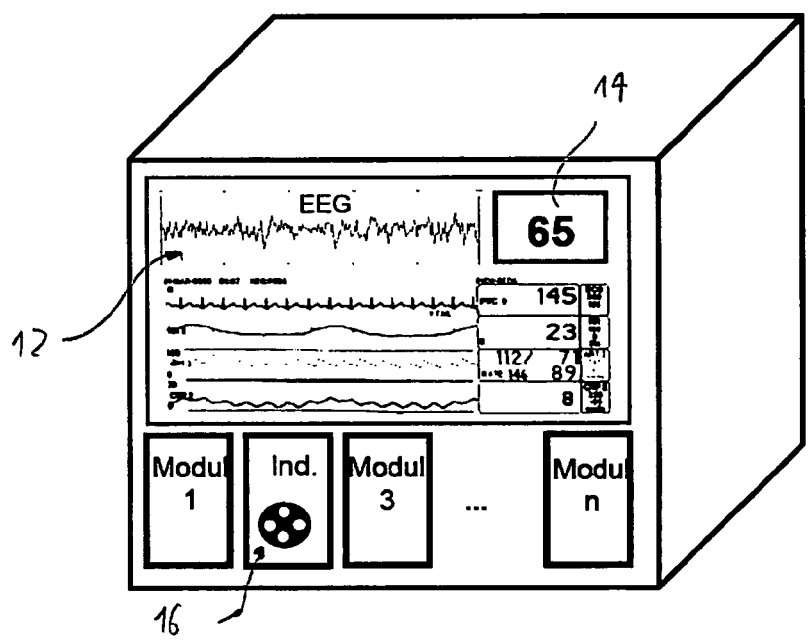

FIG. 1b shows another anaesthesia monitor 10' that is in general very similar to the monitor 10 shown in FIG. 1a. However, the anaesthesia monitor 10' consists of a conventional standard monitoring device of anaesthesia in which the functionality of determining an indicator from a plurality of parameter values is embodied in a plug-in module 16 that can be reversibly removed from and inserted into the housing of the monitor 10'. When combined with the monitor 10', the plug-in module 16 provides the same functionality as the monitor 10 shown in FIG. 1a.

Figure 2:
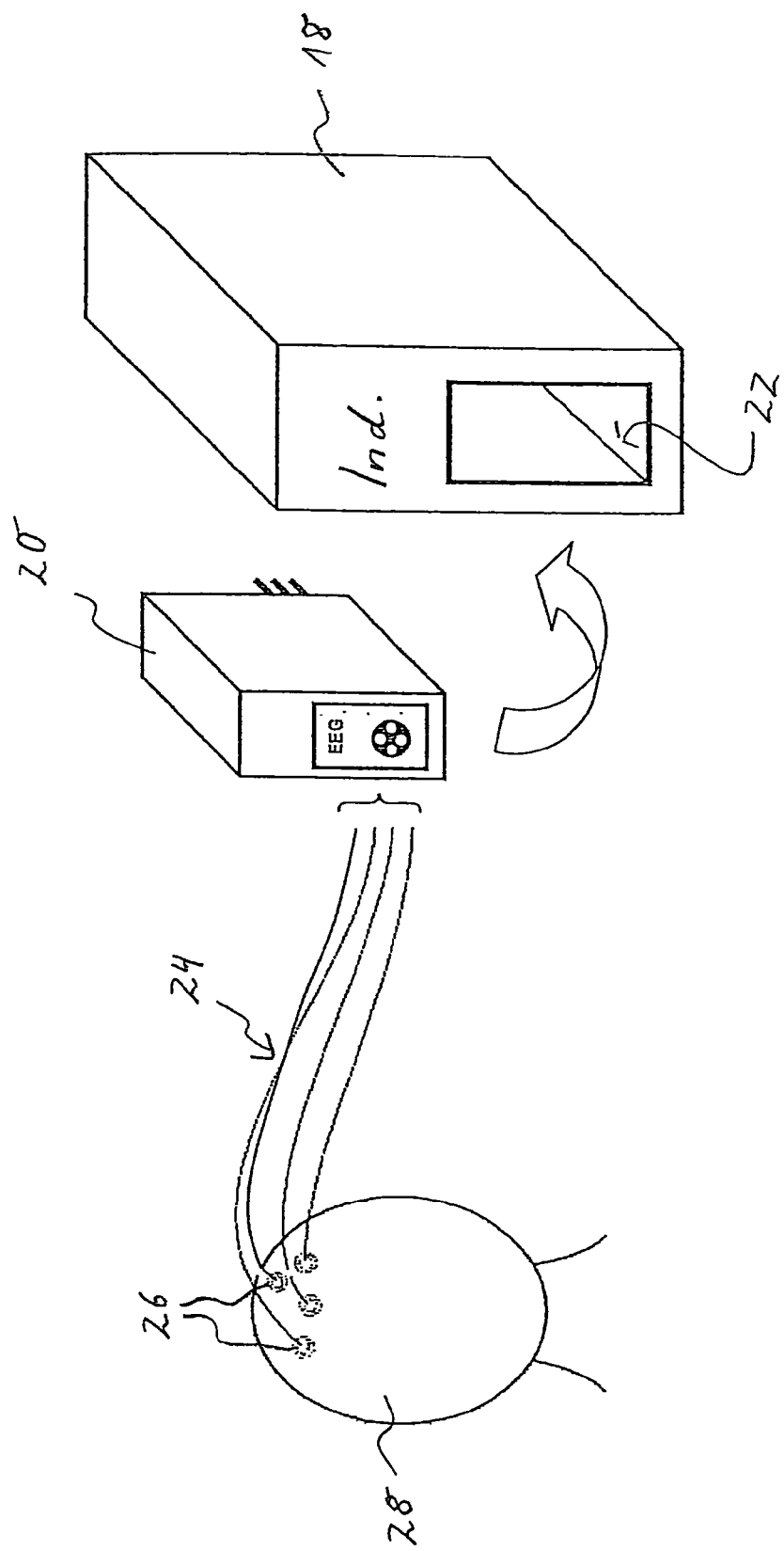
FIG. 2 shows an indicator module with a plug-in EEG amplifier that can be employed in a system for monitoring a patient and quantifying the depth of anaesthesia according to the present invention.

FIG. 2 shows an indicator module 18 which is in general similar to the plug-in indicator module 16 described with reference to FIG. 1b above. The indicator module 18 comprises a slot 22, into which an EEG amplifier module 20 can be inserted. The EEG amplifier module 20 can be connected via a set of cables 24 to a set of respective electrodes 26 attached to a head of a patient 28 for EEG data acquisition.

The EEG amplifier module 20 may be equipped with its own battery-driven power supply, so that it may be operated even when it is not inserted into the plug-in indicator module 18. This allows the EEG amplifier module 20 to be placed in the vicinity of the patient 28 without having to move the monitor device 10'. Data transport between the EEG amplifier module 20 and the indicator module 18 may be achieved by means of a wireless connection.

Anaesthesia monitors of the type shown in FIGS. 1 and 2 may be used in intensive care units or in an operating theatre to monitor anaesthesia, sedation or coma reliably and with enhanced accuracy, and in particular to accurately determine a level of anaesthesia from wakefulness to deep anaesthesia and for accurately timed detection of intraoperative awareness for different combinations of anaesthetics or sedatives, as will now be described.

The monitoring systems described with reference to FIGS. 1 and 2 may be adapted to determine an indicator value that quantifies the hypnotic component of anaesthesia and/or the analgesic component of anaesthesia based on combination of at least one EEG parameter with at least one standard parameter and/or one parameter relating to patient data and/or at least one parameter relating to the concentration of medication administered to said patient.

The EEG parameters may typically be gathered with EEG electrodes placed in the frontal and/or temporal region of the patient's head 28, wherein one to four electrodes are generally sufficient for the EEG analysis. A two-channel difference EEG with channels AT1 and/or M2 for the EEG analysis, channel Fpz for the reference and channel F7 for ground have been found to be particularly useful. Calculation of symbolic transfer entropy requires bipolar EEG with typically frontal or frontal-parietal or frontal-temporal or frontal-occipital or parietal-occipital electrode combinations. Electrodes in the parietal and the occipital region of the head 28 may give additional information for determining the indicator related to specific effects of anaesthesia on neural dynamics.

The sampling frequency of the EEG shall preferably permit an analysis of EEG frequencies up to at least 30 Hz (sampling frequency 70 Hz or higher, preferably 200 Hz), and up to 400 Hz (sampling frequency 1 kHz or higher) if electromyography (EMG) should be included in analysis.

EMG signals may be included in the analysis if desired, but may be preferably omitted for analysis of cortical activity. This can be achieved by means of low or band pass filtering of the EEG, preferably using a high cutoff frequency up to 30 Hz. Inclusion of frequencies within the EEG γ-band (above 30 Hz) such as in BIS may affect the detection of consciousness. If electrodes are positioned on the forehead, particularly γ-activity is overlapped by EMG of the frontal muscle. Therefore, such an indicator may also be a surrogate measure (muscle activity) of the hypnotic component of anaesthesia. As a consequence, a patient who is fully awake during neuromuscular block may not be detected as "awake" if no EMG is detected. Therefore, computation of the said indicator to quantify the hypnotic component of anaesthesia should preferably be independent from the EEG γ-band, which improves the signal-to-noise ratio of the target EEG analysis.

The inventors found that an analysis of the EEG data by means of an entropic quantity allows an expedient analysis of the complex EEG signal and to reliably extract the information that is most meaningful for quantifying the depth of anaesthesia. Entropic methods that were found particularly useful include the ordinal permutation entropy (PeEn) and the approximate entropy (ApEn), as described in D. Jordan et al., "Electroencephalographic order pattern analysis for the separation of consciousness and unconsciousness: An analysis of approximate entropy, permutation entropy, recurrence rate and phase coupling or order recurrence plots"; Anesthesiology, 109: 1014-1022, 2008; and B. Horn et al., "A combination of electroencephalogram and auditory evoked potentials separates different levels of anaesthesia in volunteers". Anaesthesia & Analgesia, 108 (5): 1512-1521, 2009; and D. Jordan, "Signalanalysemethoden für das EEG-Narkosemonitoring". Dissertation, Fortschritts-Berichte VDI, Reihe 17, Nr. 280, 2010.

Ordinal permutation entropy has been found to be particularly suitable for distinguishing the dynamic transition between consciousness and unconsciousness at a boundary region between these two states, whereas approximate entropy has been found particularly useful for characterising varying states of anaesthesia down to deep anaesthesia including EEG burst suppression.

Symbolic transfer entropy as described in the related patent application DE 10 2011 100 137.9 (filed on May 17, 2011 with the German Patent and Trademark Office) has also been found very useful for the analysis of EEG data. Symbolic transfer entropy may be employed to address mechanistic effects of induced unconsciousness by quantifying the cortical information flow. Since unconsciousness is directly associated with impaired information processing in the brain, this approach is well adapted for hypnosis monitoring.

The advantage of an entropic characterisation of the EEG data by means of ordinal permutation entropy or symbolic transfer entropy lies in a significant reduction of the acquisition time needed to acquire reliable data, down to below 10 seconds, as well as a reduction of the EEG frequency range to below 30 Hz. Short analysis times are particularly useful to determine quickly and reliably the state of consciousness, thereby reducing the risk of memory recall.

The reduction of the frequency band allows to reduce the influence of unwanted EMG signals.

Instead of or in addition to the entropic analysis, spectral analysis techniques, a wavelet analysis, recurrence analysis or a dimensional analysis may likewise be employed in the processing of the EEG data.

Several methods have been found suitable for combining parameters into an indicator that quantifies the "depth of anaesthesia" according to the present invention. The adaptive neuro fuzzy inference system (ANFIS) according to the so-called TSK model (named after Tagaki Sugeno Kang) has been found particularly useful.

ANFIS is an iterative optimization method employing back propagation, which allows to draw conclusions about the hypnotic and/or vigilance and/or analgesic state from logical rules and weights, wherein Gauss distribution functions are employed to associate the parameters to linguistic quantities (fuzzification). A more detailed description of the ANFIS system can be found in J. S. Jang: "ANFIS: Adaptive-Network-Based Fuzzy Inference System", IEEE Transactions on Systems, Man and Cybernetics, Vol. 23, No. 3, May 1993. The TSK model is described in further detail in T. Takagi et al., "Fuzzy identification of systems and its application to modelling and control", IEEE Transactions on Systems, Man and Cybernetics, Vol. 15, No. 1, February 1985.

However, other methods such as neural networks, support vector machines, regression or statistical relational machine learning with or without involving adaptive algorithms for online training may likewise be employed.

Basically all these methods can be extended by specific algorithms for parameter replacement and/or imputation such that they allow to reliably determine an indicator value even if the number of parameter values changes during training or during the monitoring of the patient, for instance due to failure of one or several of the sensor systems or due to insufficient signal quality which may be caused by artefacts. This allows to increase the robustness and reliability of the monitoring system beyond what can be achieved with conventional systems.

The number of parameter values may change if one of the respective sensors fails completely or provides signals of insufficient quality. The quality of the measurement values may be checked at predetermined intervals by means of an automated artefact determination. Parameters may fail in combination (such as due to a failure of the EEG sensors, which will typically affect all EEG parameters), or individually (for instance, if there is no data on the weight of the patient).

Missing values can be replaced by means of imputation, such as mean value imputation, univariate or multivariate regression based on previously acquired values, matching of the incomplete data vector with a complete data vector, or multiple imputation under consideration of the variant structure of acquired data. Techniques of this type are generally described in P. J. Garcia-Laencina et al., "Pattern classification with missing data: a review". Neural Comput & Applic., 19: 263-282, 2010.

Alternative models for generating missing values include K-nearest neighbour techniques, SOM (self-organising map) techniques, MLP (multi-layer perception) techniques, or RNN (recurrent neural network) techniques. Model-based imputation-free techniques are capable of directly integrating missing parameter values into the modelling, which can be achieved by taking every combination of available parameter values into account and employing decision-tree techniques, support vector machines, or fuzzy inferences.

Fuzzy inferences allow to replace missing parameter values with predetermined parameter ranges (intervals) or initial values.

Prediction and smoothing the indicator time series can be performed using multivariate techniques of time series prediction and forecast, e.g. Kalman filters, neuronal networks or adaptive median filters (e.g. weighted repeated median filters).

Training and analysis may be simplified considerably by employing sub-indicators to characterise selected anaesthesia states, wherein said sub-indicators are subsequently combined to a global indicator. Anaesthesia states that have been found particularly useful are the boundary region between consciousness and unconsciousness of the patient, or the level of hypnosis of said patient. Different parameter values are suitable for characterising these anaesthesia states. EEG parameters as well as a breathing gas composition, effect site/plasma concentrations and individual medication data and patient data are particularly useful to characterise the boundary region between consciousness and unconsciousness, whereas electrocardiogram data, blood pressure and other standard parameters are chosen in addition to EEG parameters, a breathing gas composition and effect site/plasma concentrations in order to determine an overall state of hypnosis.

Alternatively or additionally, the steps of computing the first and second sub-indicators may differ in terms of the underlying data set employed to compute the sub-indicators. For instance, a first sub-indicator may be determined based on a comparison of the acquired data values with a data set of previously acquired training values specifically adapted to characterize the boundary region between consciousness and unconsciousness, whereas the second sub-indicator may be computed based on a comparison with a different data set of previously acquired training data that characterizes an overall hypnosis state. For instance, the first data set employed to determine the first sub-indicator may be a large data sample that relates entirely to the crucial boundary between consciousness and unconsciousness, whereas the data set on which the computation of the second sub-indicator is based may be a data set of a comparable size, but with data distributed evenly over all the phases of hypnosis.

The two-stage procedure of determining sub-indicators first and then combining said sub-indicators to a global indicator in a subsequent step not only reduces the model complexity of determining the indicator value, thereby improving model reliability by including expert knowledge into the model design. It also provides a method and system that is more robust if one or several of the parameter values should become temporarily unavailable during the monitoring. Such a failure may result in some of the sub-indicators becoming less meaningful, but other sub-indicators will generally be less affected and will continue to provide a meaningful characterisation of the state of anaesthesia.

Figure 3:
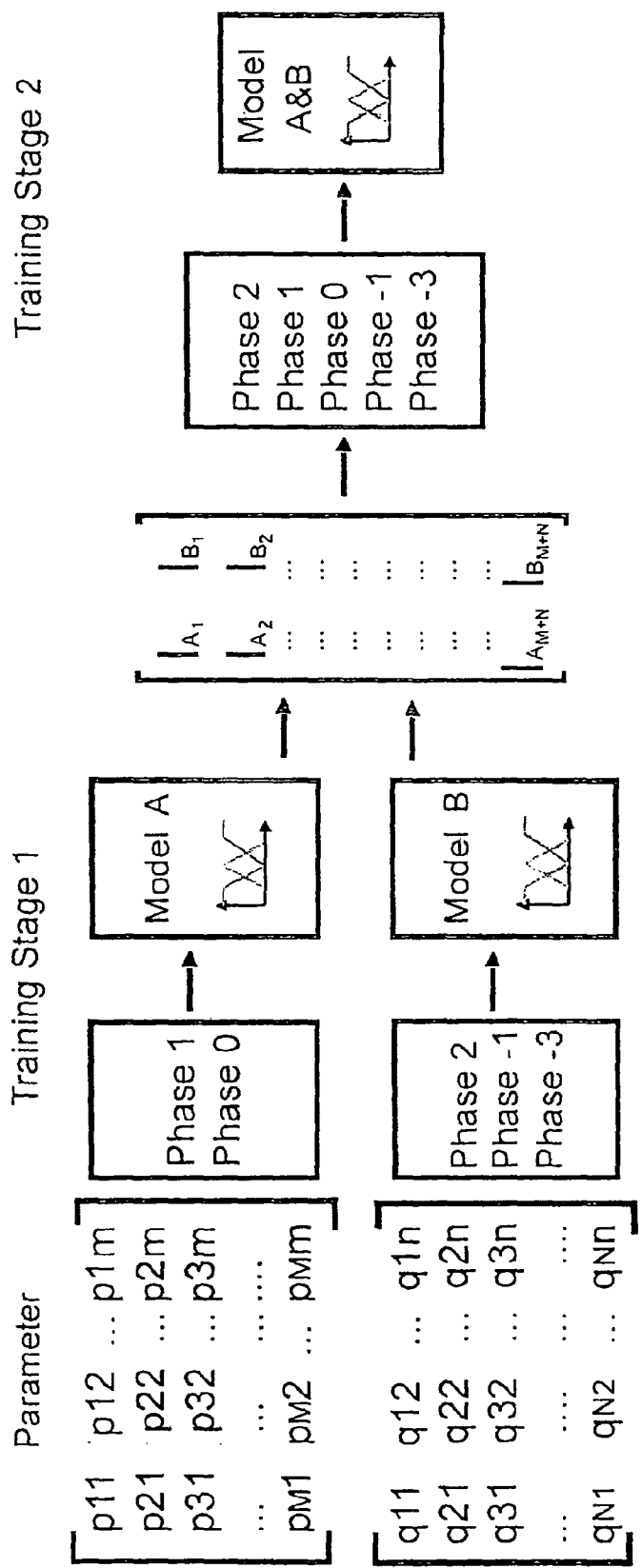
FIG. 3 illustrates how an indicator for quantifying the depth of anaesthesia according to the present invention may be established based on a training set of collected patient data in a two-stage procedure, with sub-indicators A, B that are subsequently combined to an indicator.

A two-stage procedure for determining an indicator model from training data according to the present invention is illustrated in FIG. 3. Model A in FIG. 3 corresponds to a sub-indicator for characterising the boundary between consciousness and unconsciousness, and is computed from a first subset of m parameters that may be chosen from the examples described above. Matrix $M_A$ in the upper line of FIG. 3 comprises a data set for these m parameters, gathered from M input training data samples. This data set is subjected to the TSK model to derive first indicator values $I_A$, possibly a distinct indicator value $I_A$; for each data sample in the training set.

Correspondingly, n parameter values chosen from the examples described above are selected as the second subset of parameters to characterise the level of hypnosis of said patient. Matrix $M_B$ in FIG. 3 incorporates this set of n parameters for a data sample gathered from N input training data samples, and is likewise subjected to the TSK model to generate second sub-indicators $I_B$. Again, a single indicator value $I_{BS}$ may be derived from each data sample in the training set.

These sub-indicators $I_A$ and $I_B$ are then combined to a global indicator value in a second, subsequent stage. This subsequent step may optionally comprise a further evaluation on the entire training data set incorporated into matrices $M_A$ and $M_B$. Thereby $I_A$ more reliably indicates a first aspect of anaesthesia pertaining to the choice of parameters for the first sub-indicator or the first training set, and $I_B$ dmore reliably indicates a second aspect of anaesthesia, pertaining to the choice of parameters for the second sub-indicator or the second training set. A second training procedure with respect to both paradigms A and B includes particularly designed sub-indicators instead of the full initial parameter set which supports decision making of the data driven algorithm by reducing dimension within the training process. Cross-validation can be employed to avoid overfitting of the data.

Figure 4:
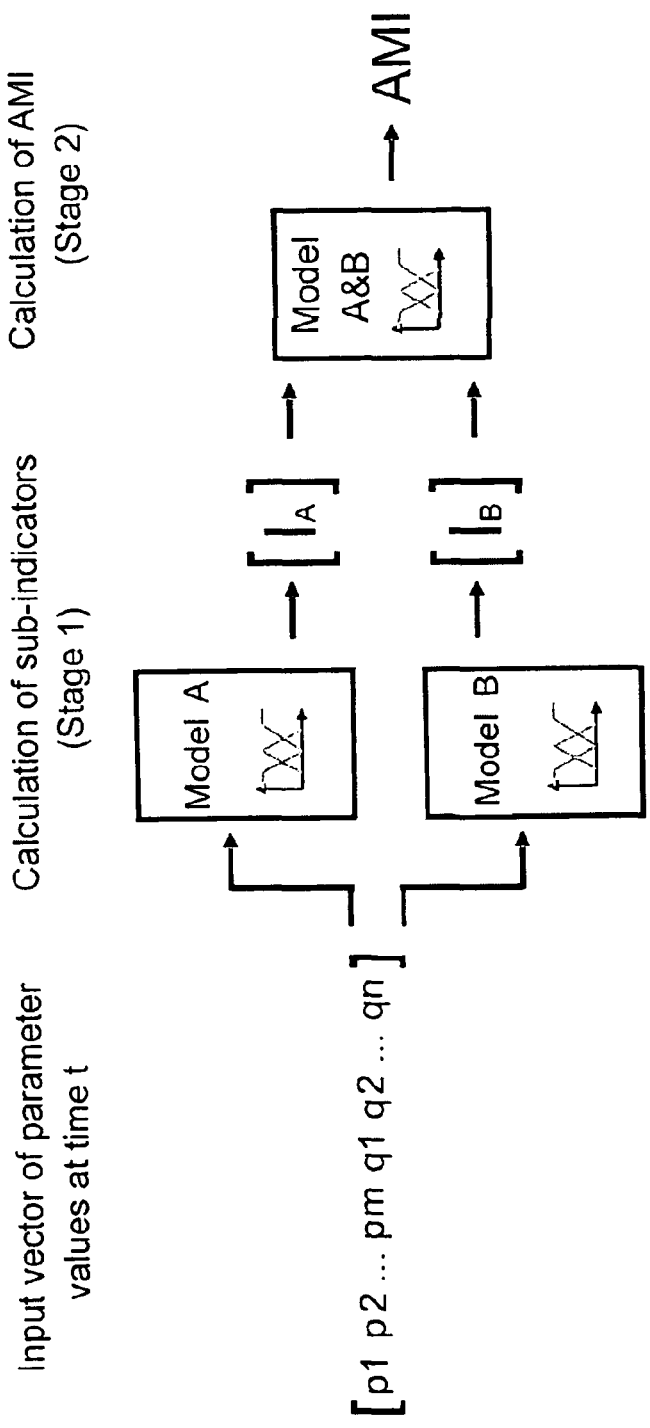
FIG. 4 illustrates a method for quantifying the depth of anaesthesia while monitoring a patient in a two-stage procedure, wherein sub-indicators A, B are determined first and are then combined to compute an indicator value related to the hypnotic component of anaesthesia and/or the analgesic component of anaesthesia.

Real-time processing of data during monitoring proceeds correspondingly and is again di-vided into two subsequent stages. As illustrated in FIG. 4, a data set comprising m+n parameters is acquired from the patient under survey at a specific point of time. The data set comprising the first subset of m parameters is employed to compute a first sub-indicator $I_A$ by means of the TSK model, whereas the second subset comprising n parameters is employed to compute the second sub-indicator $I_B$. Based on these sub-indicators, a single anaesthesia multimodal indicator (AMI) according to the present invention is determined to quantify the "depth of anaesthesia" of the patient under consideration from the set of acquired data values, where both paradigms A (e.g. the transition between consciousness and unconsciousness) and B (e.g. overall appreciation of the "anaesthetic depth") are weighted by the AMI. The two stage model $I_A$ and $I_B$ may represent specific aspects of anaesthesia as selected by the training data $M_A$ and $M_B$. Even if real time data are not separated in paradigms A and B, $I_A$ is particularly designed to indicate the aspect A and $I_B$ is particularly designed to indicate the aspect B. Therefore, considering paradigm-specific models $I_A$ and $I_B$ includes expert knowledge as much as possible for real time processing and increases the ability of the overall AMI to reflect reliably different aspects of anaesthesia.

In order to train and to test the methods and the system according to the present invention under real-life conditions, two clinical trials with 40 patients each were performed. Patients were randomly subjected to one of two groups of medication: 20 patients received the hypnotic propofol (intravenously), whereas 20 patients received sevoflurane (gaseous), both groups in combination with the opioid remifentanil for analgesia. Both trials were employed to assess the suitability of EEG parameters for distinguishing between consciousness and unconsciousness at the boundary between both states. It was found that ordinal permutation entropy and weighted spectral median frequency (WSMF) were more suitable to characterise this boundary region than the conventional bispectral index (BIS).

In a further pair of trials with 15 patients each, propofol or sevoflurane (trial 1, crossover design) and propofol or propofol/remifentanil (trial 2, crossover design) were administered in different concentrations between loss of consciousness and a state of deep anaesthesia. Deep anaesthesia was determined by means of the characteristic EEG burst suppression (BS) pattern, as described in B. Horn et al., "A combination of electroencephalogram and auditory evoked potential separates different levels of anaesthesia in volunteers". Anaesthesia & Analgesia, 108(5): 1512-1521, 2009. This approach allowed to identify EEG parameters that are suitable to provide a monotonic indication of the depth of anaesthesia from wakefulness all the way down to deep anaesthesia including EEG burst suppression. Approximate entropy was found a particularly useful parameter for this goal.

In a further trial, data from a multi-centre study (MCS) with 263 patients in six European centres was used to obtain a suitable model for determining and evaluating the AMI. Patients were associated each to one out of eleven anaesthetic combinations, consisting of opioid analgesics (remifentanil, fentanyl, sufentanil), hypnotic drugs for induction (thiopental, propofol, etomidate), and maintenance (propofol, isoflurane, sevoflurane, desflurane). Standard parameters as well as EEG parameters and AEP parameters were monitored.

While hypnosis was initiated, patients were asked to squeeze the hand of an observer every 15 seconds, wherein Tunstall's technique was employed to make sure that patients could respond to the request even when subjected to relaxants. When the request was left unanswered, patients were considered consciousless (loss of consciousness, LOC). After a skin incision was performed, further medication was administered until burst suppression (BS) was reached. The surgery then proceeded according to clinical routine. At the end of the surgery, supply of medication was stopped, and patients were again repeatedly asked to squeeze the hand of an observer to determine the return of consciousness (ROC). Trial data was gathered at the boundaries LOC and ROC, as shown in FIG. 5a. Further trial data was gathered during "awake", "clinical practice" and at BS, as shown in FIG. 5b. Both these data sets were employed for

| Standard parameters | EEG parameters | Medication | Patient data |
|---|---|---|---|
| heart rate (1 min) | ApEn (5 s) | protocol during induction and maintenance (variable, sliding window) | age (constant) |
| BP syst., dia., averaged (5 min) | PeEn (5 s) | | gender (constant) |
| gas $O_2$ insp.-exp., $CO_2$ exp., agent insp.-exp., Spiro $P_{Peak}$ (1 min) | WSMF (5 s) | | weight (constant) |
| effect site and plasma concentrations (5 s) | BS ratio (30 s measurement period, sliding window) | | |
| relative changes of the above quantities (1 min and 5 min) | | | |
| heart rate variability: $\mu$, $\sigma$ (1 min measurement period, sliding window) | | | |
| heart rate variability: ApEn, PeEn (10 min measurement period, sliding window) | | | |

The values that appear in parentheses in the above table denote the respective sampling rates (sliding window: update every 5 seconds). ApEn stands for approximate entropy, whereas PeEn denotes the ordinal permutation entropy.

In order to evaluate the model, the prediction probability ($P_K$) to distinguish between specific states of consciousness was determined according to the method described in D. Jordan et al., "A Program for Computing the Prediction Probability and the related Receiver Operating Characteristics Graph". Anesth Analg, 111(6): 1416-21, 2010. The following table shows the results obtained with the two-stage model described above ($P_K$ AMI). A comparison with the conventional BIS model ($P_K$ BIS) shows that the present invention achieves a significantly higher prediction probability (significance level<0.05 for comparison of the AMI and the BIS). The table also shows the amount of used data per class (anaesthetic state).

| | data (anesthetic levels) | # of data points | $P_K$ AMI | $P_K$ BIS | comparison |
|---|---|---|---|---|---|
| all anesthetic combinations | A conscious-unconscious | 480-526 | 0.85 (0.82-0.87) | 0.74 (0.71-0.77) | (0.07-0.14)* |
| | B awake-clinical practice-BS | 478-336-336 | 0.94 (0.93-0.95) | 0.75 (0.73-0.78) | (0.12-0.17)* |
| | B awake-clinical practice | 478-336 | 0.99 (0.98-1.00) | 0.86 (0.83-0.89) | (0.06-0.11)* |
| | A&B awake/consc.-unconsc.-clin. pract.-BS | 741-526-336-336 | 0.93 (0.92-0.94) | 0.80 (0.78-0.81) | (0.10-0.13)* |
| induction | A (propofol) conscious-unconscious | 287-293 | 0.88 (0.85-0.91) | 0.74 (0.70-0.78) | (0.09-0.18)* |
| | A (thiopental) conscious-unconscious | 73-80 | 0.77 (0.70-0.85) | 0.70 (0.61-0.78) | (−0.02-0.18) |
| | A (etomidate) conscious-unconscious | 120-153 | 0.81 (0.75-0.86) | 0.75 (0.69-0.81) | (−0.01-0.13) |
| maintenance | B (gas) awake-clinical practice-BS | 316-264-264 | 0.93 (0.92-0.94) | 0.78 (0.75-0.80) | (0.13-0.18)* |
| | B (intravenous) awake-clinical practice-BS | 130-60-60 | 0.95 (0.93-0.97) | 0.87 (0.83-0.91) | (0.03-0.12)* |
| | B (gas and intravenous) awake-clinical practice-BS | 32-12-12 | 0.92 (0.87-0.97) | 0.66 (0.52-0.79) | (0.12-0.41)* | training and test of the AMI using a threefold cross validation according to the present invention.

Based on these data sets, the following parameters were selected for determining the AMI indicator according to the present invention:

The distribution of indicator values for (i) awake/consciousness, (ii) unconsciousness, (iii) "clinical practice", and (iv) burst suppression (BS) is shown in FIG. 6a for the conventional BIS model, and in FIG. 6b for the AMI model according to the present invention.

The present invention is not limited to determining the depth of anaesthesia of a human or animal patient. It may likewise be employed to monitor the analgesic component or monitor the vigilance of a subject, e.g. during sedation in intensive care unit or during gastroenterologic examination, or to monitor sleep for applications in sleep research or to monitor the vigilance of drivers or pilots.

The detailed description of the preferred embodiments and the figures merely serve to illustrate the invention and the advantages entailed, but should not be understood to limit the invention in any sense. The scope of the invention is to be determined solely by the appended set of claims.

LIST OF REFERENCE SIGNS 10, 10' anaesthesia monitor
12 display of anaesthesia monitor
14 indicator output
16, 18 plug-in indicator modules
20 EEG amplifier module
22 slot for EEG amplifier module
24 cables
26 EEG electrodes
28 head of patient

The invention claimed is:

1. A method for quantifying at least one of anaesthesia and a state of vigilance from a plurality of parameters acquired from a subject, said method comprising the steps of:
acquiring a plurality of p parameters pertaining to said subject, said parameters being selected from a first parameter group comprising electrocardiogram data acquired from said subject, a heart rate, a heart rate variability, a blood pressure, a blood pressure variability, a breathing gas composition, a pharmacokinetic/pharmacodynamic modelled effect site concentration and/or plasma concentration, and/or a second parameter group comprising electroencephalogram data and/or auditory evoked potential data acquired from said subject, and/or a third parameter group comprising subject data and/or medication data;
wherein p≥2, and at least one of said p parameters is selected from said first parameter group or said second parameter group;
wherein said parameters of at least one of said first parameter group and said second parameter group are acquired continuously or at predetermined time intervals by monitoring said subject; and
determining an indicator that performs at least one of quantifying a depth of anaesthesia, detecting intraoperative awareness and quantifying an analgesic component of anaesthesia or a state of vigilance of said subject from said p parameters;
wherein said step of determining said indicator comprises a step of combining said p parameters, wherein said number p of parameters is variable while monitoring said subject;
wherein said step of determining said indicator comprises the steps of:
determining a first sub-indicator based on a first subset of parameters chosen among said p parameters and/or based on a comparison with a first training set of data, wherein said first sub-indicator is adapted to characterize a first aspect of an anaesthesia or vigilance state of said subject;
determining a second sub-indicator based on at least one of a second subset of parameters chosen among said p parameters and a comparison with a second training set of data, said second subset of parameters being different from said first subset of parameters and/or said second training set of data being different from said first training set of data, wherein said second sub-indicator is adapted to characterize a second aspect of an anaesthesia or vigilance state of said subject; and
combining said first sub-indicator and said second sub-indicator to compute said indicator.

2. The method according to claim 1, wherein said step of combining said p parameters comprises the step of employing one or more of an adaptive neuro fuzzy inference system, a neural network, regression, support vector machines and statistical relational machine learning.

3. The method according to claim 1, further comprising the step of replacing a parameter that becomes unavailable by means of a model-based replacement using initialized values or ranges of values, an average value imputation, univariate regression from previously recorded parameter values, multivariate regression from previously recorded parameter values, or matching of an incomplete parameter vector with a complete vector of previously recorded parameter values, or by means of a prediction employing a K-nearest neighbour model, a self-organizing map, multilayer perception, or recurrent neural network techniques.

4. The method according to claim 1, wherein at least one parameter among said p parameters is chosen from said second parameter group.

5. The method according to claim 1, wherein said first aspect is a boundary region between alertness and unconsciousness of said subject, and said first subset preferably comprises at least one of electroencephalogram data, in particular at least one of an ordinal permutation entropy computed from said electroencephalogram data and a symbolic transfer entropy computed from said electroencephalogram data, a weighted spectral median frequency computed from said electroencephalogram data, a breathing gas composition, in particular an inspiratory oxygen concentration, an expiratory oxygen concentration, an expiratory $CO_2$ concentration, an inspiratory anaesthetic gas concentration, an expiratory anaesthetic gas concentration, a pharmacokinetic/pharmacodynamic modelled effect site concentration, a plasma concentration, electrocardiogram data, an approximate entropy of a heart rate variability, an ordinal permutation entropy of a heart rate variability, subject data and medication data.

6. The method according to claim 1, wherein said second aspect is a level of anaesthesia of said subject, and said second subset preferably comprises at least one of electroencephalogram data, in particular an approximate entropy, an ordinal permutation entropy computed from said electroencephalogram data, a burst suppression ratio computed from said electroencephalogram data, a breathing gas composition, in particular an inspiratory oxygen concentration, an expiratory oxygen concentration, an expiratory $CO_2$ concentration, an inspiratory anaesthetic gas concentration, an expiratory anaesthetic gas concentration, a pharmacokinetic/pharmacodynamic modelled effect site concentration, a plasma concentration, electrocardiogram data, an approximate entropy of a heart rate variability, an ordinal permutation entropy of a heart rate variability, subject data, and medication data.

7. The method according to claim 1, wherein said step of determining said indicator comprises the step of determining a third sub-indicator based on at least one of a third subset of parameters chosen among said p parameters and a comparison with a third training set of data, said third subset of parameters being different from at least one of said first subset of parameters, and/or said second subset of parameters and/or said third training set being different from at least one of said first training set and said second training set, wherein said third sub-indicator is adapted to characterize deep hypnosis, and further comprises the step of combining said first sub-indicator, said second sub-indicator, and said third sub-indicator to compute said indicator.

8. The method according to claim 7, wherein said third subset comprises at least one of an approximate entropy computed from said electroencephalogram data, an ordinal permutation entropy computed from said electroencephalogram data, and a burst suppression ratio computed from said electroencephalogram data.

9. The method according claim 1, wherein said number p of parameters and/or the type of parameters are chosen in accordance with a type and/or dose of anaesthetic or sedative to be administered to said subject.

10. The method according to claim 1, further comprising a step of recording at least one parameter value among said p parameter values and/or at least one sub-indicator value among said sub-indicator values and/or said indicator value, and/or raw input data, in particular recording at least one time-synchronized predefined event and/or free text comment if said indicator value is detected not to correspond to a clinically evaluated patient state and/or if a predefined event occurs during surgery.

11. The method according to claim 1, further comprising the step of employing at least one of said p parameters and raw input data acquired by monitoring said subject to modify an algorithm upon which said step of determining said indicator is based.

12. A system for quantifying at least one of anaesthesia and a state of vigilance from a plurality of parameters acquired from a subject, said system comprising:
  acquisition means adapted to acquire a plurality of p parameters pertaining to said subject, said parameters being selected from at least one of a first parameter group, a second parameter group, and a third parameter group, wherein said first parameter group comprises at least one of electrocardiogram data acquired from said subject, a heart rate, a heart rate variability, a blood pressure, a blood pressure variability, a breathing gas composition, a pharmacokinetic/pharmacodynamic modelled effect site concentration and plasma concentration, wherein said second parameter group comprises at least one of electroencephalogram data and auditory evoked potential data acquired from said subject, and wherein said a third parameter group comprises at least one of subject data and medication data;
  wherein p≥2, and at least one of said p parameters is selected from said first parameter group or said second parameter group;
  wherein said acquisition means are adapted to acquire said parameters of at least one of said first parameter group and said second parameter group continuously or at predetermined time intervals; and
  calculation means adapted to determine from said p parameters an indicator that quantifies a depth of anaesthesia and/or detects intraoperative awareness and/or quantifies an analgesic component of anaesthesia or a state of vigilance of said subject;
  characterized in that said acquisition means are adapted to acquire a number p of parameters that varies while monitoring said subject, and said calculation means are adapted to determine said indicator by combining said number p of parameters that varies while monitoring said subject;
  wherein said calculations means are adapted to:
    determine a first sub-indicator based on a first subset of parameters chosen among said p parameters and/or based on a comparison with a first training set of data, wherein said first sub-indicator is adapted to characterize a first aspect of an anaesthesia or vigilance state of said subject;
    determine a second sub-indicator based on at least one of a second subset of parameters chosen among said p parameters and a comparison with a second training set of data, said second subset of parameters being different from said first subset of parameters and/or said second training set of data being different from said first training set of data, wherein said second sub-indicator is adapted to characterize a second aspect of an anaesthesia or vigilance state of said subject; and
    combine said first sub-indicator and said second sub-indicator to compute said indicator.

13. The system according to claim 12, wherein at least one of said acquisition means and said calculation means are adapted to implement a method, said method comprising the steps of:
  acquiring the plurality of p parameters pertaining to said subject, said parameters being selected from the first parameter group, and/or the second parameter group, and/or the third parameter group; and
  determining the indicator from said p parameters.

14. A storage device with computer-readable instructions stored thereon, wherein the computer-readable instructions are adapted to be used on a computer for controlling a system according to claim 12.

15. A method for quantifying at least one of anaesthesia and a state of vigilance from a plurality of parameters acquired from a subject, said method comprising the steps of:
  acquiring a plurality of p parameters pertaining to said subject, said parameters being selected from a first parameter group comprising electrocardiogram data acquired from said subject, a heart rate, a heart rate variability, a blood pressure, a blood pressure variability, a breathing gas composition, a pharmacokinetic/pharmacodynamic modelled effect site concentration and/or plasma concentration, and/or a second parameter group comprising electroencephalogram data and/or auditory evoked potential data acquired from said subject, and/or a third parameter group comprising subject data and/or medication data;
  wherein p≥2, and at least one of said p parameters is selected from said first parameter group or said second parameter group;
  wherein said parameters of at least one of said first parameter group and said second parameter group are acquired continuously or at predetermined time intervals by monitoring said subject; and
  determining an indicator that performs at least one of quantifying a depth of anaesthesia, detecting intraoperative awareness and quantifying an analgesic component of anaesthesia or a state of vigilance of said subject from said p parameters;
  wherein said step of determining said indicator comprises a step of combining said p parameters, wherein said number p of parameters is variable while monitoring said subject; and
  wherein said step of combining said p parameters comprises the step of employing one or more of an adaptive neuro fuzzy inference system, a neural network, regression, support vector machines and statistical relational machine learning.

\* \* \* \* \*